United States Patent
Pechersky

(10) Patent No.: US 9,320,576 B2
(45) Date of Patent: Apr. 26, 2016

(54) THERAPEUTICALLY COUNTOURED, COMPLIANCE ENCOURAGING ALIGNER IMPLEMENT

(71) Applicant: David A. Pechersky, Aspinwall, PA (US)

(72) Inventor: David A. Pechersky, Aspinwall, PA (US)

(*) Notice: Subject to any disclaimer, the term of this patent is extended or adjusted under 35 U.S.C. 154(b) by 0 days.

(21) Appl. No.: 14/310,451

(22) Filed: Jun. 20, 2014

(65) Prior Publication Data

US 2015/0079532 A1    Mar. 19, 2015

Related U.S. Application Data

(60) Provisional application No. 61/877,656, filed on Sep. 13, 2013.

(51) Int. Cl.
*A61C 7/08*  (2006.01)
*A61C 7/36*  (2006.01)

(52) U.S. Cl.
CPC .... *A61C 7/08* (2013.01); *A61C 7/36* (2013.01)

(58) Field of Classification Search
CPC ............. A61C 7/08; A61C 7/36; A61Q 11/00
See application file for complete search history.

(56) References Cited

U.S. PATENT DOCUMENTS

| | | | | |
|---|---|---|---|---|
| 3,071,476 | A | * | 1/1963 | Werft et al. ............. 604/890.1 |
| 3,422,184 | A | * | 1/1969 | Bouchal et al. .............. 424/48 |
| 4,149,815 | A | * | 4/1979 | Kawam ....................... 401/201 |
| 4,482,321 | A | | 11/1984 | Tabor et al. |
| 4,532,126 | A | * | 7/1985 | Ebert et al. ................. 427/2.18 |
| 4,654,005 | A | | 3/1987 | Woelfel |
| 4,813,872 | A | | 3/1989 | Knitter |
| 4,828,820 | A | * | 5/1989 | Glass et al. .................... 424/48 |
| 5,087,460 | A | * | 2/1992 | Cherukuri ................ A23G 4/02 |
| | | | | 426/5 |
| 5,236,721 | A | * | 8/1993 | Yung Chu et al. ................ 426/5 |
| 5,921,255 | A | * | 7/1999 | Garita ............................ 132/329 |
| 5,970,981 | A | * | 10/1999 | Ochel ....................... A61F 5/58 |
| | | | | 128/859 |
| 6,083,527 | A | | 7/2000 | Thistle |
| 6,161,260 | A | | 12/2000 | Flewitt |
| 6,231,337 | B1 | | 5/2001 | Boyd |
| 6,244,269 | B1 | * | 6/2001 | Tyler ...................... A61F 5/566 |
| | | | | 128/859 |
| 6,458,149 | B1 | | 10/2002 | Peters-Combs |
| 6,482,395 | B1 | * | 11/2002 | Barth ....................... A61K 8/19 |
| | | | | 424/440 |
| 6,582,731 | B1 | | 6/2003 | Kaufmann |
| D500,908 | S | * | 1/2005 | Hare ............................. 426/104 |

(Continued)

OTHER PUBLICATIONS

Dentsply International, "Dentsply Raintree Essix", Chewies webpage, Oct. 23, 2011, 1 p., Sarasota, FL.

(Continued)

*Primary Examiner* — Ralph Lewis
(74) *Attorney, Agent, or Firm* — The Webb Law Firm

(57) ABSTRACT

Described is an orthodontic aligner implement that can ensure the accuracy and efficiency of clear aligner orthodontic therapies as well as increase patient compliance by reducing discomfort and combining functionality into a breath-freshening medium. The implement includes a consumable mass having at least two channels disposed on opposite sides of the mass and traversing the width of the mass. The channels are adapted to seat between opposing anterior or incisor teeth. Also described is a method of positioning an orthodontic aligner into a prescribed position that includes placing the aligner approximately in the prescribed position in one's mouth, placing the aligner implement described above into the mouth, and applying the implement in contact with the aligner in one's mouth.

9 Claims, 5 Drawing Sheets

(56) References Cited

U.S. PATENT DOCUMENTS

| | | |
|---|---|---|
| 7,147,466 B1 | 12/2006 | Hilliard et al. |
| 7,165,907 B2 * | 1/2007 | Levy .......................... 401/183 |
| 7,766,370 B2 | 8/2010 | Putcha |
| 7,806,688 B2 | 10/2010 | Knutson |
| D638,518 S | 5/2011 | Herre et al. |
| 8,287,275 B2 | 10/2012 | Knutson |
| 8,431,150 B2 | 4/2013 | Stawski et al. |
| 8,776,729 B2 * | 7/2014 | Koo et al. ...................... 119/710 |
| 2006/0257331 A1 | 11/2006 | Dulin |
| 2008/0160473 A1 | 7/2008 | Li et al. |
| 2009/0277461 A1 * | 11/2009 | Gallagher, Jr. ..... A46B 11/0003 128/861 |
| 2010/0304325 A1 | 12/2010 | Fletcher |
| 2013/0130199 A1 | 5/2013 | Palm |
| 2014/0277135 A1 * | 9/2014 | DeLaurier ............... A61J 17/00 606/236 |
| 2014/0295052 A1 * | 10/2014 | Elliott .................. A01K 15/026 426/656 |

OTHER PUBLICATIONS

Werner, A., "Acceleration by Vibration", article at www.OrthodonticProductsOnline.com, Nov. 2011, 2 pgs., Orthodontic Products, USA.

* cited by examiner

THERAPEUTICALLY COUNTOURED, COMPLIANCE ENCOURAGING ALIGNER IMPLEMENT

CROSS REFERENCE TO RELATED APPLICATION

This application claims priority to U.S. Provisional Patent Application No. 61/877,656 filed Sep. 13, 2013, the entire contents of which are herein incorporated by reference.

BACKGROUND OF THE INVENTION

1. Field of the Invention

The invention relates to a method of and device for ensuring the accuracy and efficiency of clear aligner orthodontic therapies as well as increasing patient compliance by reducing discomfort and combining functionality into a breath-freshening medium.

2. Description of Related Art

"Clear aligner therapy" can be defined as any treatment which relies on the continuous wearing of a clear plastic shell, or template, which corresponds to a specific alignment of the dentition that does not quite match the wearer's current alignment, in an effort to improve dental alignment. There are multiple custom fabricated clear aligner therapies available to clinicians. Examples of these include, but are not limited to, Invisalign®, ClearCorrect™, Simpli5™, etc. These therapies are "custom fabricated" because of the precision technology that goes into creating a sequence of aligners which are capable of guiding the progression of alignment in a desirable manner. Clear aligner therapy includes treatment for an individual who recently completed orthodontic therapy of any kind and has been given an Essix® retainer to prevent "relapse." Essix® retainers are clear plastic shells, provided after braces are removed in order to maintain alignment and occlusal correction post-treatment. "Relapse" refers to any movement of the dentition in a direction away from ideal alignment and usually towards the individual's original malocclusion; this is usually a result of non-compliance with wearing the prescribed retainer. Any relapse of the dentition's alignment will prevent the template from seating fully on the teeth. However, until complete loss of fit occurs, it is sometimes possible to recapture the alignment corresponding to the template with full time wear and some chewing exercises. If this is the prescribed course of treatment, the retainer then becomes a clear aligner.

The processes which can re-align a relapsed dentition are the same as those employed in the previously mentioned clear aligner therapies. Even with recent technological advances in the fabrication of the sequence of aligners, the success of these therapies, much like an attempt at re-alignment via the use of an Essix® retainer, is almost purely reliant on patient cooperation and compliance with the prescribed treatment regimen. Common compliance issues are due to inconvenience, soreness, and bad breath. When compliance is lacking, the first given sequence of aligners is rarely enough to achieve the desired alignment, and the result is a loss of "tracking" somewhere within the given sequence of aligners. Tracking refers to the ability of the given sequence of aligners to keep pace with the simulated and prescribed tooth movement. Any inequity of the computer simulation to the biology and capacity of the individual's teeth to move at the prescribed rate may cause a loss of tracking; or, as previously stated, a simple lack of wearing the aligners as prescribed may also result in a loss of tracking. Even if patient compliance is exemplary, sometimes a loss of tracking will occur if the computer simulation is somehow not reflective of the actual biology and/or ability of the individual's teeth to move at the expected (prescribed) rate. It is sometimes possible to recapture desired tracking by extending the wear time of the aligner which displays the poor tracking; however, without an implement to augment the action of the poorly tracking aligner, it is rarely successful.

When a loss of tracking occurs to the extent that the remaining unused aligners are unusable, using the Invisalign® system as an example, a "refinement" is ordered. A refinement is a new sequence of aligners delivered with the starting point being the current and improved alignment (the result of the first sequence of aligners given up until they no longer were effective) and an end point typically consistent with the originally prescribed end point. Three refinements are included in the initial lab fee paid for by the treating doctor. It is sometimes necessary to exhaust these refinements to satisfy a patient's expectations. The combination of additional refinements and a lengthy, unanticipated treatment time is extremely costly. My use of the terms "clear aligner therapy" and "aligner therapy" is intended also to include such additional refinements involving a new sequence of aligners. The inventor is not aware of aligners that are other than clear, but it is possible that colored aligners may at some point be offered. The applicability of my invention would of course not be affected by a colored, translucent, or opaque aligner and therefore I intend for the definition of "aligner" and "clear aligner" as used herein to include such possible variants.

The typical course of treatment for any clear aligner is for full time wear, except while eating and brushing (or around 22 hours per day as indicated on the Invisalign® website). Advice is given to brush after each meal before placing aligners back onto the teeth. It is not always feasible to follow this advice, and even if it were, food and odors remain in the mouth even after thorough brushing and flossing.

It would be in the best interest of both the treating doctor and the patient to have an auxiliary apparatus which could, with proper use, decrease treatment times and improve patient satisfaction and clinical outcomes. Another advantageous feature of such an apparatus would be seamless integration into the lifestyle of the individual using it, as this would promote compliance. Until now, a few of the available options for such an apparatus included "Chewies™" and "Acceledent®". "Chewies™" are rubberized cotton rolls which are intended to seat aligners up over the dentition in order to ensure proper fit and "action." "Action" refers to the flexing of an aligner over the dentition, creating the intended forces necessary for tooth movement into the intended alignment. The use of "Chewies™" is widely prescribed within the orthodontic and general dental profession when clear aligner therapy is provided. "Continued action" is action repeated over extended periods of time.

Moreover, the purpose and necessity of "Chewies" is often lost on a patient because of the foreign nature of the rubbery cotton roll. It is also lost on treating doctors due to expense and an often justified skepticism that the patient will use them. Aligner wearers as well as adolescents wearing Essix® retainers often report bad breath as a reason for non-compliance during the day while they are either at work or school. Furthermore, custom fabricated clear aligner therapies are most appealing due their ability to blend into everyday life. This is not often possible for business professionals, students, or anybody who leads a social and active lifestyle. Thus the orthodontist must address motivation and social relationships from the patient's perspective as part of his or her prescribed treatment.

Acceledent® is a technology which is based on a great deal of research to prove that vibratory action on the dentition during tooth movement can have an acceleratory effect. It consists of a horseshoe shaped arch made of rubber which is connected to an apparatus that sends a vibrating current through the rubber arch. When placed in the mouth between the top and bottom teeth, for 20 minutes daily, treatment times are reported to decrease by ~50%. The problem with Acceledent® is that it is often cost-prohibitive.

Conventional breath freshening implements are not suitable for use during aligner therapy. Many have convexities to them which often cause them to slip out from within the teeth. Others are flat and, due to the "teetering" effect of a flat object between two opposing points of contact, apply laterally-focused forces onto the aligners instead of vertical "seating" forces. Seating of an aligner refers to the compression of the aligner onto the teeth which is often what applies the prescribed directional forces. Salivary lubrication can also cause them to slip out while attempting to keep them between the teeth. These shortcomings are magnified when aligners are worn due to the smooth and rounded nature of their exterior.

Continued action is difficult to attain with contemporary available therapies. It would be beneficial to all parties involved to have an implement that would promote patient compliance as well as effect tooth movement in a manner aspired to by "Chewies" and Acceledent®, thereby reducing patient and clinician's costs, and improving results and patient satisfaction. The implement for doing so will be embodied by the invention described hereinafter.

SUMMARY OF THE INVENTION

The present invention offers an improved device and method by which clinicians providing, and individuals undergoing, clear aligner therapy (as previously defined) can ensure improved compliance and outcomes. The present invention is particularly advantageous due to the need for continued action (as previously defined) of the aligners over the teeth in order to achieve timely and predictable results.

The invention comprises a multi-concave implement that preferably contains xylitol and flavoring for placement in the mouth, to be used repeatedly to seat a clear aligner and provide a continuity of determined nudging, or action, of the aligner onto the dentition. These three distinct characteristics of the implement are further described below.

The multi-concave structure of the implement, characterized by at least one and preferably two sets of opposing grooves or channels, provides a quickly understood incentive for the patient to place it between his or her teeth and work it. The therapy is not only readily adopted, but the implement is easy to maintain in the proper position, thereby encouraging its use. The concavities act as guidance for the incisor teeth to reproducibly find a comfortable resting spot without much mental focus or thinking about what is being done. Furthermore, the implement can be specifically designed to fit comfortably between the teeth in a variety of orientations.

In a preferred embodiment of the invention, each aligner implement contains at least 0.5 gram xylitol. Xylitol is a sugar alcohol, like sorbitol; both are common refined sugar substitutes, cannot be metabolized by oral bacteria, and are the science behind the claim "sugarfree" or "sugarless". Furthermore, xylitol has been proven to inhibit cavity-causing bacteria (S. Mutans) from forming acid. It is often prescribed (in lozenge or gum form) to high-risk individuals during preventive and maintenance therapy as well as orthodontic therapy in an effort to avoid decalcification of the dentition. Sorbitol, as well as synthetic sweeteners, may be substituted. Any sugar substitute, or a mixture of sugar substitutes, which cannot be metabolized by oral bacteria may be used, but xylitol is preferred.

The breath freshening quality of mint has long been available to the public and has been a staple in any number of stores and in the media. Mint can include other variations of mint, such as spearmint and peppermint. It is this familiarity and prevalence in society that will enable it to be readily accepted by patients. In recent years, many other flavors have been developed for the freshening of one's breath. The implement described herein may use these other flavors as well, which include, but are not limited to, fruit flavorings and cinnamon. For many if not most patients, the entire experience of clear aligner therapy seems strange or unnatural if not grossly intrusive, and accordingly a pleasant or at least familiar feature such as mint flavoring greatly enhances acceptability. The edible quality of a mint or other flavored implement makes it an ideal vehicle to deliver both enjoyment and functionality. Combinations of the above-mentioned flavors may also be used.

The protective aspect of the implement is something that directly correlates to the mission statements of custom fabricated clear aligner therapies: the ability to maintain proper hygiene and dental health due to the ability to remove the aligners at any time.

The multi-functionality of the invention is one characteristic that makes it truly unique. To be able to freshen one's breath, protect one's teeth, and at the same time improve upon treatment duration, patient comfort, and outcome is something that no other auxiliary to clear aligner therapy can claim.

DETAILED DESCRIPTION OF THE PREFERRED EMBODIMENTS

Figure 1:
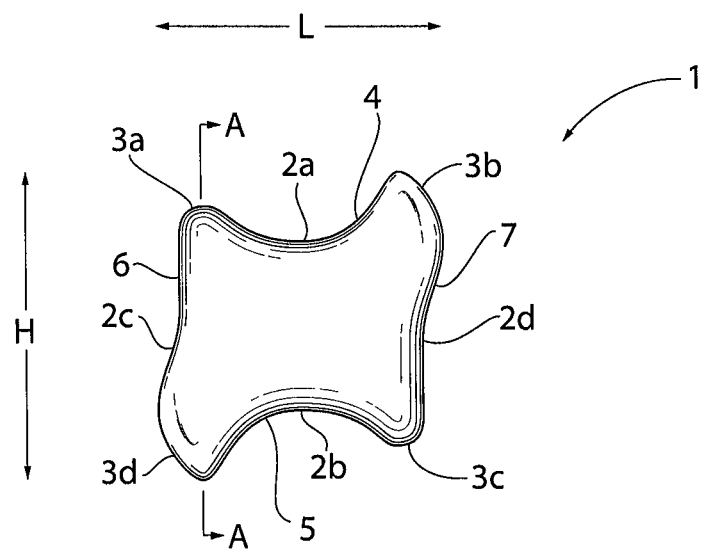
FIG. 1 is a front elevation view of an implement according to a first embodiment of the invention.
Figure 2:
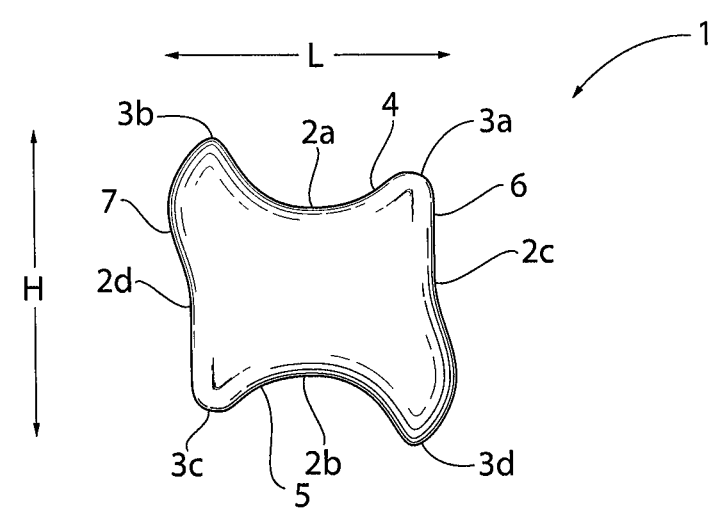
FIG. 2 is a rear elevation view of the implement of FIG. 1.
Figure 3:
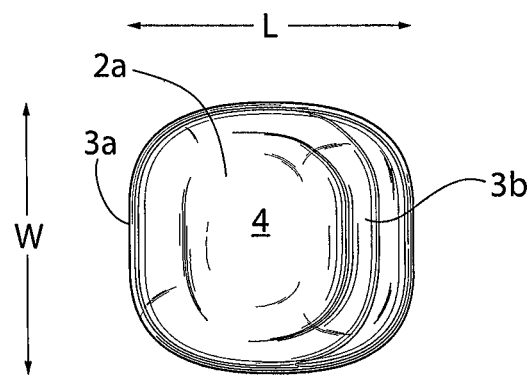
FIG. 3 is a top plan view of the implement of FIG. 1.
Figure 4:
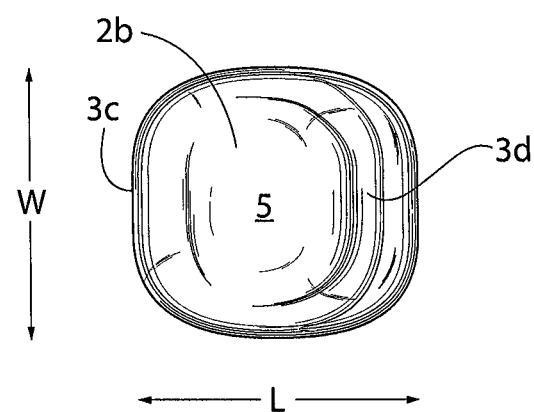
FIG. 4 is a bottom plan view of the implement of FIG. 2.
Figure 5:
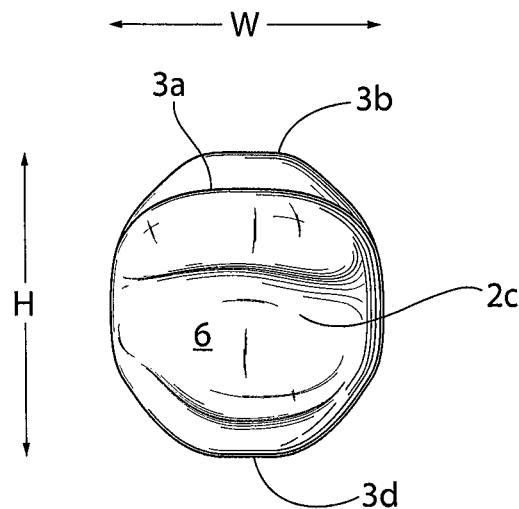
FIG. 5 is a left side elevation view of the implement of FIG. 1.
Figure 6:
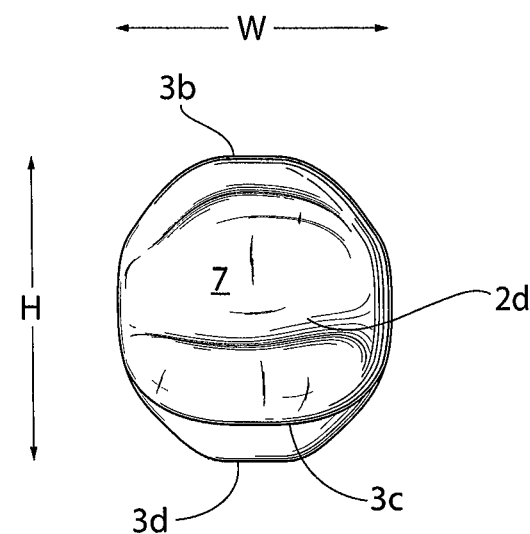
FIG. 6 is a right side elevation view of the implement of FIG. 1.
Figure 7:
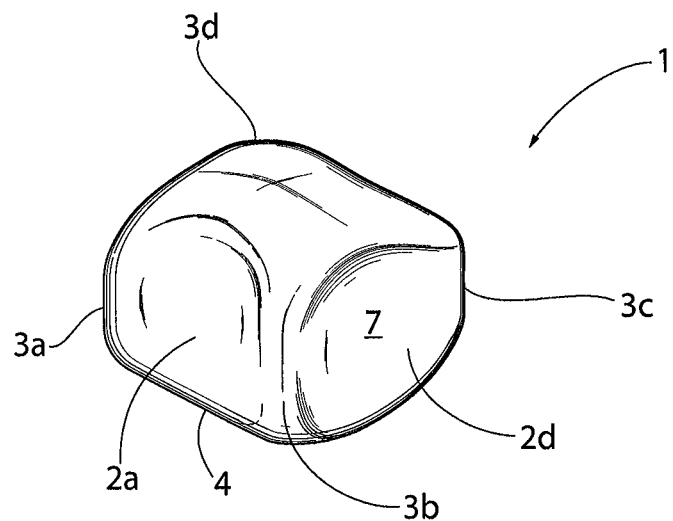
FIG. 7 is a perspective view of the implement of FIG. 1.

As used herein, spatial or directional terms, such as "left," "right," "above," "below," "top," "bottom," and the like, relate to the implement as it is shown in FIG. 1 unless otherwise noted. However, it is to be understood that the implement may assume various alternative orientations and, accordingly, such terms are not to be considered as limiting. Further, as used herein, all numbers expressing dimensions, physical characteristics, and the like, used in the specification and claims are to be understood as being modified in all instances by the term "about."

Referring now to FIGS. 1-7, a first embodiment of implement 1 is shown. Implement 1 is preferably a one-piece construction having a length dimension L, a height dimension H, and a width dimension W. The ratio of the length dimension L to the height dimension H can be 1:1 or near 1:1, in which case implement 1 has a generally square cross-section taken along line A-A of FIG. 1. Implement 1 also includes a plurality of concave channels 2a-d extending across the width dimension W, and preferably across the entire width dimension W. Channels 2a-d are generally provided in sets of two with each channel 2a-d in the set disposed on an opposite side of implement 1 from the other channel 2a-d of the set such that each channel 2a-d in the set can be used to engage with either the top or bottom teeth of a patient, as described further herein. For example, implement 1 can include a top channel 2a disposed on a top surface 4 of implement 1 and extending across the width dimension W and a bottom channel 2b disposed on a bottom surface 5 of implement 1 which is opposite top channel 2a in the height dimension H. Bottom channel 2b also extends across the width dimension W, and preferably across the entire width dimension W, of implement 1 and is generally parallel to top channel 2a. Top channel 2a and bottom channel 2b may be slightly offset with respect to one another in the length dimension L. In other words, bottom channel 2b may not be directly below top channel 2a, though it is generally positioned below top channel 2a. However, in some non-limiting embodiments, bottom channel 2b is directly below top channel 2a.

Implement 1 can include other channels 2c-d, preferably provided in oppositely-disposed sets of two, as well. For example, each of left and right side surfaces 6, 7 of implement 1 can include a concave channel 2c-d that extends across the width dimension W, and possibly across the entire width dimension W. Left side channel 2c on left side surface 6 is generally disposed opposite right side channel 2d on right side surface 7 in the length dimension L, though they can be offset from one another. As shown in FIG. 1, left side channel 2c is slightly below right side channel 2d in the height dimension H. Offsetting of the channels 2a-d can create the "N" or "Z" (depending on the orientation) shape of the implement 1 depicted in FIG. 1. Preferably, the side surface channels 2c, 2d are smaller and less deep than top and bottom channels 2a, 2b, for reasons that will become apparent below. Additional channels can be provided as well, though the preferred arrangement involves two sets of channels (for a total of four) as depicted in FIG. 1.

Implement 1 can also include a plurality, and preferably four, protrusions or arms 3a-3d, with each disposed at a respective one of the corners of implement 1 and extending in the width dimension W of implement 1, and preferably across the entire width dimension W. In FIGS. 1-7, each protrusion is depicted as an elongate, smoothly-curvatured member integral with the remainder of implement 1 and generally located at a corner of implement 1. In this embodiment, each channel 2a-d is formed between two protrusions 3a-d. In other words, with reference to FIG. 1, if one were to trace the perimeter of implement 1, one would encounter channel 2a, protrusion 3b, channel 2d, protrusion 3c, etc. Implement 1 is not intended to be limited to only the arrangement shown in FIG. 1 which includes four protrusions 3a-d, though the number of protrusions generally corresponds to the number of channels. Thus, by way of example, if implement 1 is designed with six channels, implement may also include six protrusions with each channel being formed between two protrusions.

The shape of protrusions 3a-d can vary with respect to one another, meaning that, within the same implement 1, there can exist protrusions of multiple shapes and/or sizes. With reference to FIGS. 1-7, depicted are four protrusions 3a-d, with two protrusions 3a, 3c having the same first shape and two protrusions 3b, 3d having the same second shape, where the first and second shapes differ from one another. With reference to FIG. 1, the first and second shapes alternate in the clockwise direction such that the top left protrusion 3a and bottom right protrusion 3c are similarly shaped while the top right protrusion 3b and bottom left protrusion 3d are similarly shaped. In other words, if one were to trace the perimeter of implement 1 in the clockwise direction, one would encounter protrusion 3a of a first shape, protrusion 3b of a second shape, protrusion 3c of the first shape, and then protrusion 3d of the second shape. With this configuration, the view of implement 1 depicted in FIG. 1 would remain unchanged if the implement 1 were rotated 180° about an axis that passes through implement 1 in the width dimension W. With reference to FIG. 1, it can also be said that if the implement 1 is divided in half along an axis passing through implement 1 in the height dimension H, the left side is an inverted equal of the right side. This symmetry can help ensure that each side of implement 1 dissolves evenly during use and thus remains highly functional throughout use.

Some possible, non-limiting dimensions of implement 1 of this embodiment are: Overall length, i.e., the length dimension L, can be between approximately 8 and 12 mm, such as between 10.5 and 11.5 mm. Overall height, i.e. the height dimension H, can be between 8 and 13 mm, such as between 11 and 12.5 mm. As mentioned above, the ratio of length dimension L to height dimension H (L:H) is generally near 1:1, such as between 0.8:1 and 1.1:1. Overall width, i.e. the width dimension W, can be between approximately 8 and 13 mm, such as between 10.5 and 12 mm. The length of top and bottom channels 2a, 2b, which extend in the width dimension W, can be between approximately 8 and 13 mm, such as between 11 and 12 mm. The space between the peaks of protrusions 3a and 3b, and likewise between the peaks of protrusions 3c and 3d, can be between approximately 5 and 8 mm, such as between 6.5 and 8 mm. The channels 2a-d should be sufficiently wide to accommodate a patient's tooth while still allowing sufficient room for the tooth to be slid back and forth along the arch of channel 2a-d to work the implement 1. The average front to back width of an incisor is about 1.0-1.5 mm; therefore, in the most severe of malalignment where two teeth were literally overlapping one another, channel widths of between 3 and 6 mm, such as between 4.5 and 6 mm, would be accommodating. Protrusions 3b and 3d can extend beyond protrusions 3a and 3c in the height dimension H by an amount of, for example, 1 to 2 mm, such as 1 to 1.5 mm. Overall depth of the channels 2a-d as measured from the top of the smaller protrusion (e.g., protrusion 3a in FIG. 1) can be between 1.2 and 2.6 mm, such as between 1.9 and 2.6 mm, with top and bottom channels 2a, 2b generally having greater depth than left and right channels 2c, 2d. The generally elongate, smoothly contoured form with channels may be maintained while any or all of the noted useful dimensions are varied by plus or minus fifteen percent. Implements within these dimensions will be adequate to accommodate almost any malalignment. However, a smaller implement 1 may have insufficient strength and be more susceptible to premature cracking during use. Further, implements can be developed with different sizes to accommodate patients with different sized teeth. For example, implements having dimensions near the bottom of the recited range may be appropriate for women, children, and young adults whereas implements having dimensions near the top of the recited range may be more appropriate for men.

Figure 8:
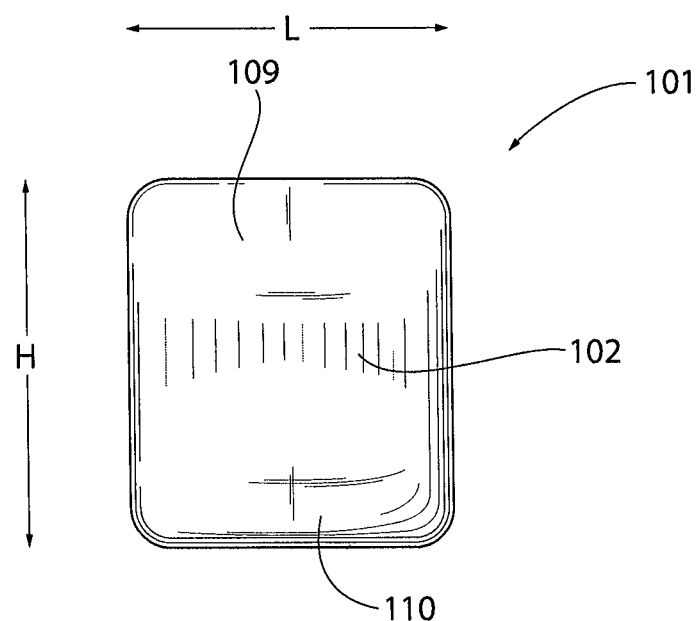
FIG. 8 is a top plan view of an implement according to a second embodiment of the invention.

Referring now to FIG. 8, a second embodiment of the implement 101 is seen to have a generally elongate, smoothly curvatured, form including a top channel 102 across its length L. In this overhead view, it is seen that top channel 102 is not in the middle of the width W of the implement 101, but is structured between a lip side 109 and a tongue side 110 which has more mass than the lip side 109. The implement 101 of this embodiment is otherwise generally symmetrical in that there is another channel, not seen, parallel to top channel 102 on the underside. Thus the view from the underside is substantially identical to FIG. 8. However, it should be understood that top channel 102 need not be exactly over the opposite channel, but rather could be slightly offset but still generally parallel while still preserving the mass relationship of the lip side 109 and tongue side 110—that is, the tongue side is larger. The generally elongate form of implement 101 may be said to have an axis through its length L, and the two channels also may be said to have axes (not illustrated) substantially parallel to the implement axis. The channels and the implement as a whole may, however, be slightly curved, with the lip side 109 being on the convex side of the curve.

Some useful, non-limiting dimensions of implement 101 of this embodiment are: Overall length, and length of channel 102 and its underside counterpart, 14 mm; width at the tops of the channels, 4 mm, and width of the implement at its center, 9 mm. The average front to back width of an incisor is about 1.0-1.5 mm; therefore, in the most severe of malalignment where two teeth were literally overlapping one another, the channels would be accommodating. The generally elongate, smoothly contoured form with channels may be maintained while any or all of the noted useful dimensions are varied by plus or minus fifteen percent. That is, the length may vary from 11.9 to 16.1 mm, the width may vary from 7.6 to 10.35 mm, and the depth of one or both channels may vary from 1.7 to 2.3 mm, for example. Implements within these dimensions will be adequate to accommodate almost any malalignment, it being understood that the mass of the tongue side 110 will remain larger than the mass of the lip side 109.

Figure 9:
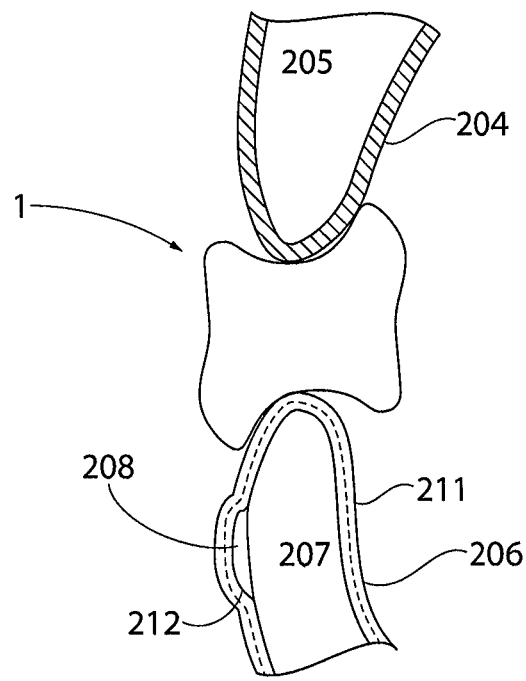
FIG. 9 is a side sectional view of the implement of FIG. 1 in a typical position in a patient's mouth.
Figure 10:
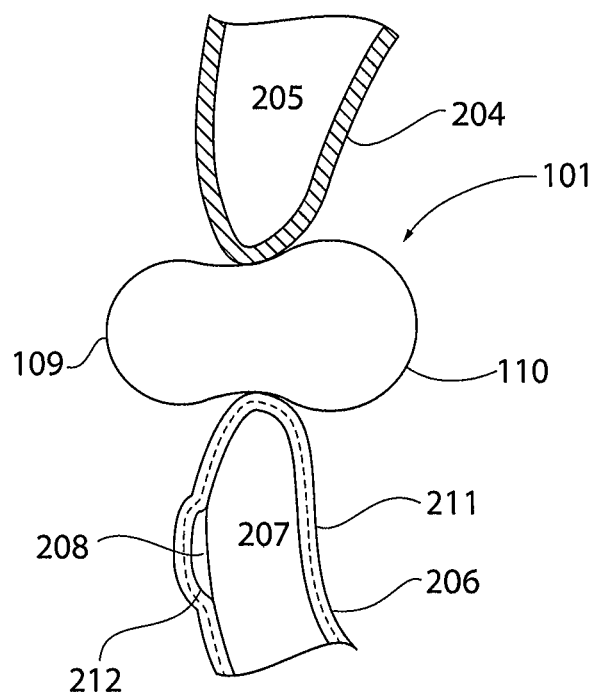
FIG. 10 is a side sectional view of the implement of FIG. 8 in a typical position in a patient's mouth.

FIGS. 9-10 depict a section through the front of a patient's mouth with implement 1, 101 applied for working. A retainer 204 covers upper (maxillary) tooth 205. An attachment 208 adheres to lower (mandibular) tooth 207. Aligner 206 generally follows the contour of lower tooth 207 without necessarily conforming to its surface. Implement 1, 101 is placed between the upper and lower teeth—that is, between retainer 204 and aligner 206, such that upper tooth (or teeth) 205 and lower tooth (or teeth) 207 engage with the channels 2a-d, 102. The patient then "works" the implement by sliding his or her teeth along the arches created by channels 2a-d, 102. Working the implement 1, 101 between the teeth in this position places a downward force on the aligner 206, providing the necessary action to move aligner 206 approximately into the position represented by dotted line 211. A cycle of action would consist of compression and release, where the aligner 206 is in the position indicated by dotted line 211 during compression. The cycles of compression and release are important because this is when the prescribed directional forces are created. The force may be exerted upon compression or release, depending on the prescribed tooth movement. In FIGS. 9-10, the bevel 212 is designed to allow the aligner 206 to hang from it upon release and, in doing so, apply a specific directional force.

Implement 1, 101 can be arranged in a number of different orientations while in patient's mouth. Selection of the appropriate orientation is largely up to the patient and based on what fits or feels the best for the patient. Considerations as to what is most effective may also play a role, but the feel or fit is of primary concern as a comfortable feel will best ensure the patient works implement 1, 101 for the appropriate amount of time.

For example, looking first to the first embodiment, implement 1 can be arranged in the patient's mouth with top channel 2a oriented upward such that it engages upper tooth 205 and bottom channel 2b oriented downward such that it can engage lower tooth 207. Implement 1 could also be arranged in the exact opposite orientation, with bottom channel 2b oriented upward and engaging upper tooth 205 and top channel 2a oriented downward and engaging lower tooth 207. Assuming top and bottom channels 2a, 2b have approximately the same dimensions, as is the case in FIG. 1, each of these two orientations would produce essentially the same effect and feeling for patient. However, if there are slight differences in the dimensions of top and bottom channels 2a, 2b, each of these two orientations would produce a slightly different feel. By way of another example, implement 1 can be arranged in the patient's mouth with left channel 2c oriented upward such that it engages upper tooth 205 and right channel 2d oriented downward to engage lower tooth 207. The opposite orientation, with right channel 2d oriented upward, is also possible. Again, assuming left and right channels 2c, 2d have approximately the same dimensions, as in FIG. 1, each of these two orientations would produce the same feel for the patient. However, because left and right channels 2c, 2d generally have less depth than top and bottom channels 2a, 2b, orienting implement 1 with top channel 2a or bottom channel 2b engaging top tooth 207 would produce a different feel for patient than if right channel 2d or left channel 2c were to engage top tooth 207. Particularly, if top and bottom teeth engage the less deep left and right channels 2c, 2d, the incisors (or other teeth engaging the implement 1) would rest in a more open position due to the additional bulk of the implement 1 between the teeth. "Open" refers to the level of closure of the jaw, which, in this scenario, is determined by the thickness of material between the incisor teeth. In a more open position, the jaw-closing muscles (masseter, temporalis, and medial pterygoid) are more relaxed; therefore, it may be desirable to maintain a more open position. By including channels of varying depth, the patient is given more options to find the best fit for implement 1. Further, as mentioned above, due to the symmetry of implement 1, implement 1 can dissolve in a consistent manner while maintaining its cross-sectional architecture and, therefore, functionality.

With respect to the second embodiment, implement 101 can be arranged with the lip side 109 forward and the tongue side 110 oriented toward the interior of the mouth. Patient can then engage top channel 102 with upper tooth 205 and bottom channel with lower tooth 207. Implement 101 can also be flipped along its elongated axis such that top channel 102 engages lower tooth 207.

The channels 2a-d, 102 are important for the clear aligner therapy, particularly with respect to incisor and anterior alignment therapies. Because of the implement's contour and multiple dimensions in different directions, the patient is able to work the implement 1, 101 back and forth as well as in cycles of compression and release, according to his or her specific alignments and relative misalignments. The channels 2a-d, 102 are adapted to seat between opposing teeth in the anterior or incisor areas. The channels 2a-d, 102 can span the entire width of implement 1, 101, extending from one side to the other, and are important to its application in the anterior, or incisor area, of the arch, where anterior-posterior (front-to-back) width is minimal and it is difficult to maintain anything between the teeth. The incentive to bite on and chew the implement 1, 101 is enhanced by the enticing mint flavoring and the xylitol additive.

Further, the shape of protrusions 3a-d, is also important to the application of implement 1. The protrusions 3a-d assist in maintaining implement 1 in place between the teeth while it is worked back and forth by acting as a barrier that prevents the tooth from slipping out of the arch of channel 2a-d. The shape of protrusions 3a-d should further this purpose but one should not create intrusive bulk or cumbersome mobility within the mouth while working implement 1 along the arch. In use, the smaller protrusions 3a, 3c, are generally positioned on the tongue side of the lower teeth because the anterior teeth are not smooth all the way to the gum line like as is the case on the lip side of the anterior teeth due to the cingulum on each tooth.

The implement 1, 101 is constructed to provide resiliency sufficient for the implement to maintain its shape after repeated chewing and working in the seat between opposing teeth. It will break down after varying time periods, depending on two kinds of variables, namely those relating to the structure and composition of the implement, and those determined by the vagaries of chewing force, frequency of cycles, and composition of the patient's saliva. Although I do not intend to be bound to any particular longevity for a single implement, a useful duration period is three to five minutes of chewing and working (continued action), during which the flavoring and the xylitol are released. The implement may have a hard but chewable coating to assure that its shape will be maintained over a desired period of time.

It should be understood that the multi-concave nature of implement 1, 101, characterized by opposing grooves or channels, provides a quickly understood incentive for the patient to place it between his or her teeth and work it. The therapeutic aspects of the implement are not only readily adopted, but the implement is easy to maintain in the proper position, thereby encouraging its use. The benefits or motivations for using any auxiliary implement are important in understanding the likelihood of compliance. For example, a few of the possible benefits or motivations for using implement with aligner therapy are the following:

The implement makes aligner therapy more enjoyable.
The implement improves the efficiency of aligner therapy.
Because the aligner therapy is more efficient, treatment times are reduced, which is beneficial to both the patient and the provider.
Clinical outcomes are improved.
Discomfort associated with aligner therapy is alleviated.
Greater patient satisfaction with aligner therapy benefits the provider as well as the patient.
Because of increased efficiency of treatment, costs are reduced.
The implement facilitates the integration of aligner therapy into the everyday lifestyle of the patient. Use of implement may be quite discreet compared to prior art therapies which require conspicuously grasping a handle or stem by hand to keep a chewing device in place.

Chewies™, through experience, do not make aligner therapy more enjoyable mainly due to their need to be cleaned and re-used, as well as the additional hand that is needed to keep one in place throughout its use. Furthermore, requiring the use of Chewies™ does not improve the integration of aligner therapy into everyday life. Acceledent® has been reported to be easier to integrate into treatment due to its extremely high frequency of vibration and therefore only twenty minutes per day usage. However, it vastly increases costs for both the clinician and patient. All of the above benefits and advantages are present in my invention, which, in addition, is simple and inexpensive.

The implement's composition and construction are preferably intended to allow both the flavoring and the coherent mass to last for approximately 3-5 minutes. The minimum recommended protocol for usage of each implement is to apply two implements, one after the other in sequence, for approximately 3-5 minutes each, following the insertion of an aligner. To "apply" the implement means to work (gently chew) one or more implement(s) in succession around the dentition for approximately 3-5 minutes following the insertion of an aligner. This will ensure that each time the aligners are taken out, presumably to eat and/or brush, and placed back in the mouth, they are given the proper action that is required to achieve desired results. Continued usage (continued action) of the implements throughout treatment, above and beyond the minimum recommended protocol, can shorten treatment time an estimated 15-25% (currently based on empirical evidence and clinical experience).

Notwithstanding the utility of an implement having a longevity of 3-5 minutes under gentle chewing as described above, the durability of a single implement is not important to accomplish the goals of both breath-freshening and superior functionality. Rather, it is most important that the patient apply continued action for a daily total of at least 30 minutes.

The implement is consumable, meaning that it may be swallowed and is digestible. Desirable ingredients for making a consumable mass include magnesium stearate as a filling agent, one or more flavoring extracts, such as mint, xylitol, preferably with calcium lactate as a carrier, gum arabic as a binding agent, and camuba wax for a hard crust or shell. Sodium CMC, or cellulose gum, may also be used as a binder or filler. All of these ingredients may be swallowed and digested. Ingredients and methods used to make a consumable mass suitable for the present invention are generally known in the art, such as in U.S. Pat. No. 8,431,150 to Stawski et al., U.S. Pat. No. 6,582,731 to Kaufmann, and U.S. Pat. No. 6,083,527 to Thistle, each of which is herein incorporated by reference.

Generally, the proportions of the ingredients are selected so that the implement may be worked for at least three minutes without breaking up; however, a particular life span of a single implement is not critical for the therapy, which is designed around a prescribed daily performance of continued action. The number of implements consumed in a day is not as important as a range of cycles of continued action. The patient may prefer to work implement for only a minute or less; this is satisfactory so long as the number of implements per day is increased accordingly.

Thus, described is an orthodontic aligner implement comprising a consumable mass including channels on opposite sides and traversing the width of the mass, the channels being adapted to seat between opposing anterior or incisor teeth. Also described is a method of positioning an orthodontic aligner into a prescribed position comprising (a) placing the aligner approximately in the prescribed position in one's mouth, (b) placing an aligner implement into the mouth, and (c) applying said implement in contact with the aligner in one's mouth. It also includes a method of promoting the acceleration of tooth movement in a patient undergoing clear aligner therapy comprising prescribing for the patient a regimen including successively applying a plurality of aligner implements of between the upper and lower teeth soon after each placement of the aligner implement in the mouth, for a total of at least 30 minutes in a day.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

The invention claimed is:

1. A method of positioning an orthodontic aligner into a prescribed position comprising: (a) placing said aligner at least approximately in the prescribed position in one's mouth; (b) placing an aligner implement into the mouth, wherein the aligner implement comprises a consumable mass having a top side and a bottom side opposite the top side, wherein each of the top side and the bottom side includes a single channel traversing the width of said mass, said channels being adapted to seat between opposing anterior or incisor teeth; (c) positioning the aligner implement such that opposing anterior or incisor teeth are seated within said channels; and (d) with said implement positioned as in step (c), applying pressure between said implement and said aligner.

2. The method of claim 1 comprising performing the applying of step (d) for at least three minutes.

3. The method of claim 1 further comprising repeating steps (b), (c), and (d) with a second aligner implement, wherein the second aligner implement comprises a consumable mass having a top side and a bottom side opposite the top side, wherein each of the top side and the bottom side includes a single channel traversing the width of said mass, said channels being adapted to seat between opposing anterior or incisor teeth.

4. The method of claim 1 wherein said applying is performed for 3-5 minutes.

5. The method of claim 1 further comprising repeating steps (b), (c), and (d) with one or more additional aligner implements, wherein each of the one or more additional aligner implements comprises a consumable mass having a top side and a bottom side opposite the top side, wherein each of the top side and the bottom side includes a single channel traversing the width of said mass, said channels being adapted to seat between opposing anterior or incisor teeth, so that the total contact time between said aligner implements and said aligner is at least 30 minutes in a day.

6. A method of promoting the acceleration of tooth movement in a patient undergoing clear aligner therapy comprising prescribing for said patient a regimen including:
   a) placing an aligner at least approximately in a prescribed position in the patient's mouth;
   (b) placing an aligner implement into the patient's mouth, wherein the aligner implement comprises a consumable mass having a top side and a bottom side opposite the top side, wherein each of the top side and the bottom side includes a single channel traversing the width of said mass, said channels being adapted to seat between opposing anterior or incisor teeth;
   (c) positioning the aligner implement such that opposing anterior or incisor teeth are seated within said channels; and
   (d) with said implement positioned as in step (c), applying pressure between said implement and said aligner.

7. The method of claim 6 wherein said aligner implement includes at least 0.5 grams of a sweetener which cannot be metabolized by oral bacteria.

8. The method of claim 7 wherein said sweetener is xylitol.

9. The method of claim 6 wherein said aligner implement includes mint flavoring in an, amount sufficient to last at least three minutes while pressure is being applied in step (d).

* * * * *